(12) United States Patent
Lee et al.

(10) Patent No.: US 10,442,741 B2
(45) Date of Patent: Oct. 15, 2019

(54) CHROMIUM COMPOUND, CATALYST SYSTEM INCLUDING SAME, AND METHOD FOR TRIMERIZING ETHYLENE USING THE CATALYST SYSTEM

(71) Applicant: AJOU UNIVERSITY INDUSTRY-ACADEMIC COOPERATION FOUNDATION, Suwon-si, Gyeonggi-do (KR)

(72) Inventors: Bun Yeoul Lee, Suwon-si (KR); Jong Yeob Jeon, Chungcheongnam-do (KR); Dong Sik Park, Suwon-si (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/123,878

(22) PCT Filed: Mar. 4, 2015

(86) PCT No.: PCT/KR2015/002067
§ 371 (c)(1),
(2) Date: Sep. 6, 2016

(87) PCT Pub. No.: WO2015/133805
PCT Pub. Date: Sep. 11, 2015

(65) Prior Publication Data
US 2017/0217854 A1    Aug. 3, 2017

(30) Foreign Application Priority Data

Mar. 5, 2014  (KR) .................. 10-2014-0026270
Jan. 9, 2015  (KR) .................. 10-2015-0003639

(51) Int. Cl.
| | |
|---|---|
| C07C 2/32 | (2006.01) |
| B01J 31/12 | (2006.01) |
| C07F 11/00 | (2006.01) |
| B01J 31/14 | (2006.01) |
| B01J 31/22 | (2006.01) |
| B01J 31/18 | (2006.01) |

(52) U.S. Cl.
CPC .............. *C07C 2/32* (2013.01); *B01J 31/12* (2013.01); *B01J 31/143* (2013.01); *B01J 31/181* (2013.01); *B01J 31/2265* (2013.01); *C07F 11/00* (2013.01); *B01J 2231/12* (2013.01); *B01J 2231/20* (2013.01); *B01J 2531/0205* (2013.01); *B01J 2531/31* (2013.01); *B01J 2531/62* (2013.01); *C07C 2531/14* (2013.01); *C07C 2531/22* (2013.01)

(58) Field of Classification Search
None
See application file for complete search history.

(56) References Cited

U.S. PATENT DOCUMENTS

| | | | |
|---|---|---|---|
| 5,376,612 A | 12/1994 | Reagen et al. | |
| 5,563,312 A | 10/1996 | Knudsen et al. | |
| 5,856,257 A | 1/1999 | Freeman et al. | |
| 2010/0030000 A1* | 2/2010 | Emoto | C07C 2/32 585/512 |

FOREIGN PATENT DOCUMENTS

| | | |
|---|---|---|
| JP | 10-36435 A | 2/1998 |
| WO | 99/19335 A1 | 4/1999 |

OTHER PUBLICATIONS

Dixon et al., "Advances in selective ethylene trimerisation—a critical overview", Journal of Organometallic Chemistry, vol. 689, pp. 3641-3668, (2004).
Makhaev et al., "Mechanochemical Synthesis of Chromium Tris(2-ethylhexanoate) and Evaluation of Its Catalytic Activity in the Reaction of Ethylene Trimerization", Russian Journal of Applied Chemistry, vol. 86, No. 12, pp. 1819-1824, (2013).
Vidyaratne et al., "Isolation of a Self-Activating Ethylene Trimerization Catalyst", Angew. Chem. Int. Ed., vol. 48, pp. 6552-6556, (2009).

* cited by examiner

*Primary Examiner* — Yun Qian
(74) *Attorney, Agent, or Firm* — Vorys, Sater, Seymour & Pease LLP; Mih Suhn Koh

(57) ABSTRACT

Disclosed herein are a chromium compound represented by Formula 1a or 1b and a catalyst system including the same, exhibiting superior catalytic activity in an olefin trimerization reaction:

$[\{CH_3(CH_2)_3CH(CH_2CH_3)CO_2\}_2Cr(OH)]$      [Formula 1a]

$[\{CH_3CH_2CH(CH_2CH_3)CO_2\}_2Cr(OH)]$.      [Formula 1b]

5 Claims, 4 Drawing Sheets

CHROMIUM COMPOUND, CATALYST SYSTEM INCLUDING SAME, AND METHOD FOR TRIMERIZING ETHYLENE USING THE CATALYST SYSTEM

TECHNICAL FIELD

Embodiments of the present invention relate to a chromium compound, a catalyst system including the same, and a method of trimerizing ethylene using the catalyst system.

BACKGROUND ART

In 1994, Philips presented a catalyst system for preparing 1-hexene, etc. by trimerizing olefins, such as ethylene, particularly, a highly active and selective ethylene trimerization catalyst system using a trivalent chromium compound, a pyrrole compound, a non-hydrolyzed aluminum alkyl, and an aromatic hydrocarbon (unsaturated hydrocarbon) (U.S. Pat. No. 5,376,612). Subsequently, based on the catalyst system, 1-hexene has been commercially produced since 2003. Among various trivalent chromium compounds, a catalyst system using tris(2-ethyl hexanoate) chromium (III) ($Cr(EH)_3$, $EH=O_2C_8H_{15}$) exhibited superior catalytic activity. A catalyst system using $Cr(EH)_3$ has been intensively researched and commercialized.

In the case of the catalyst system using $Cr(EH)_3$, an aromatic hydrocarbon solvent may be prepared by, for example, adding a mixture of triethylaluminum and ethylaluminum dichloride to an aromatic hydrocarbon solvent (toluene, etc.), as a mixture of $Cr(EH)_3$ and 2,5-dimethylpyrrole. In general, since trimerization of olefins is carried out in an aliphatic hydrocarbon solvent such as cyclohexane, an aromatic hydrocarbon solvent of a prepared catalyst system is removed through vacuum suction and then the aromatic hydrocarbon solvent-removed catalyst system is re-dissolved in an aliphatic hydrocarbon solvent such as cyclohexane. Alternatively, the catalyst system using the prepared aromatic hydrocarbon is used in a trimerization reaction and, after terminating the trimerization reaction, the aromatic hydrocarbon solvent used to prepare the catalyst is isolated and removed. In addition, when a catalyst is prepared using $Cr(EH)_3$, a catalytic activation species is formed and thus a black precipitate is generated as a by-products, whereby a process of filtering the black precipitate is required (see U.S. Pat. No. 5,563,312). Such processes of removing and filtering an aromatic hydrocarbon solvent, such as toluene, may be a roadblock to commercialization. When the catalyst system is prepared in an aliphatic hydrocarbon solvent, such as cyclohexane, in which trimerization occurs, to omit the process of removing an aromatic hydrocarbon solvent, thermostability of a prepared catalyst is decreased. Accordingly, a catalyst is inactivated during trimerization reaction or catalyst selectivity is decreased, thus by-products, other than trimers, are generated in a large amount (see U.S. Pat. No. 5,563,312). Accordingly, in catalyst systems, etc. manufactured by Philips, aromatic hydrocarbons (unsaturated hydrocarbons) are included as essential components.

Therefore, there is a need for development of a raw material compound which does not cause the production of by-products upon preparation of a catalyst and thus does not require a filtration process, etc. and allows the preparation of a catalyst system in an aliphatic hydrocarbon solvent, and a catalyst system exhibiting superior catalytic activity upon ethylene trimerization.

DISCLOSURE

Technical Problem

Therefore, the present invention has been made in view of the above problems, and it is an object of the present invention to provide a chromium compound having a novel structure.

It is another object of the present invention to provide a catalyst system which allows a simple catalyst preparation process, exhibits superior catalytic activity upon an ethylene trimerization reaction, and includes the chromium compound.

It is still another object of the present invention to provide an ethylene trimerization reaction using the catalyst system.

The above and other objects can be accomplished by the present invention described below.

Technical Solution

An embodiment of the present invention relates to a chromium compound represented by any one of Formulas 1a and 1b below:

[{$CH_3(CH_2)_3CH(CH_2CH_3)CO_2$}$_2$Cr(OH)], and [Formula 1a]

[{$CH_3CH_2CH(CH_2CH_3)CO_2$}$_2$Cr(OH)]. [Formula 1b]

The chromium compound may include a compound represented by Formula 1c below:

[{$CH_3(CH_2)_3CH(CH_2CH_3)CO_2$}$_2$Cr(OH)]$_4$·$2H_2O$ [Formula 1c]

Another embodiment of the present invention relates to a catalyst system including a reaction product of a chromium compound; an aluminum compound; and a pyrrole compound, or an alumino-pyrrole compound.

The catalyst system of the embodiment may include a reaction product of:
a chromium compound represented by Formula 1 below;
an aluminum compound represented by Formula 3 below; and
a pyrrole compound represented by Formula 4 below:

($R^1CO_2$)$_2$Cr(OH) [Formula 1]

wherein $R^1$ is a $C_3$ to $C_{30}$ alkyl group or a $C_6$ to $C_{40}$ aryl group;

($R^2$)$_n$Al($X^2$)$_{3-n}$ [Formula 3]

wherein $R^2$ is a $C_1$ to $C_{20}$ hydrocarbon group, $X^2$ is a halogen atom, and an average value of n is 1 to 3; and

[Formula 4]

$$\begin{array}{c} H \\ | \\ N \\ R^6 \diagup \diagdown R^3 \\ | \quad\quad | \\ R^5 \quad R^4 \end{array}$$

wherein $R^3$, $R^4$, $R^5$, and $R^6$ are each independently a hydrogen atom or a $C_1$ to $C_{10}$ alkyl group.

In an embodiment of the catalyst system, the chromium compound represented by Formula 1 may be a compound represented by any one of Formulas 1a and 1b below:

[{$CH_3(CH_2)_3CH(CH_2CH_3)CO_2$}$_2$Cr(OH)], and [Formula 1a]

[{$CH_3CH_2CH(CH_2CH_3)CO_2$}$_2$Cr(OH)]. [Formula 1b]

In an embodiment of the catalyst system, the chromium compound represented by Formula 1 may be a compound represented by Formula 1c below:

[Formula 1c]

The aluminum compound may be a mixture of triethylaluminum ($Et_3Al$) and diethylaluminumchloride ($Et_2AlCl$) and the pyrrole compound represented by Formula 4 is 2,5-dimethylpyrrole.

In an embodiment of the catalyst system, a molar ratio of the chromium compound to the aluminum compound (Cr:Al) added upon preparation (reaction) may be 1:10 to 1:50.

In an embodiment of the catalyst system, a molar ratio of the chromium compound to the pyrrole compound (chromium compound:pyrrole compound) added upon preparation (reaction) may be 1:1 to 1:5.

In another embodiment, the catalyst system may include a reaction product of:

a chromium compound represented by Formula 1c below;

an aluminum compound represented by Formula 3 below; and an alumino-pyrrole compound represented by Formula 5 below:

[Formula 1c]

[Formula 3]

wherein $R^2$ is a $C_1$ to $C_{20}$ hydrocarbon group, $X^2$ is a halogen atom, and an average value of n is 1 to 3; and

[Formula 5]

wherein $R^2$ is a $C_1$ to $C_{20}$ hydrocarbon group and $R^3$, $R^4$, $R^5$, and $R^6$ are each independently a hydrogen atom or a $C_1$ to $C_{10}$ alkyl group.

The aluminum compound is a mixture of triethylaluminum ($Et_3Al$) and diethylaluminumchloride ($Et_2AlCl$), the alumino-pyrrole compound represented by Formula 5 is a compound represented by Formula 5 wherein $R^2$ is an ethyl group, $R^3$ and $R^6$ are methyl groups, and $R^4$ and $R^5$ are hydrogen atoms.

In another embodiment of the catalyst system, a molar ratio of the chromium compound to the aluminum compound (Cr:Al) added upon preparation (reaction) may be 1:10 to 1:50.

In another embodiment of the catalyst system, a molar ratio of the chromium compound to the alumino-pyrrole compound (chromium compound:alumino-pyrrole compound) added upon preparation (reaction) may be 1:1 to 1:5.

In another embodiment, the catalyst system may include a catalyst precursor represented by Formula 2 below; and an aluminum compound represented by Formula 3 below:

[Formula 2]

wherein $R^2$ is a $C_1$ to $C_{20}$ hydrocarbon group, X is $R^2$ or a halogen atom, and $R^3$, $R^4$, $R^5$, and $R^6$ are each independently a hydrogen atom or a $C_1$ to $C_{10}$ alkyl group, and

[Formula 3]

wherein $R^2$ is a $C_1$ to $C_{20}$ hydrocarbon group, $X^2$ is a halogen atom, and an average value of n is 1 to 3.

In Formula 2, $R^2$ may be a methyl or ethyl group, X may be $R^2$ or a chlorine atom, $R^3$ and $R^6$ may be methyl groups, and $R^4$ and $R^5$ may be hydrogen atoms.

The aluminum compound may be a mixture of triethylaluminum ($Et_3Al$) and diethylaluminumchloride ($Et_2AlCl$).

In the mixture, a molar ratio of the catalyst precursor to the aluminum compound (Cr:Al) may be 1:10 to 1:50.

Another embodiment of the present invention relates to a catalyst precursor represented by Formula 2 below. The catalyst precursor represented by Formula 2 below is the same as the catalyst precursor represented by Formula 2 described above:

[Formula 2]

wherein $R^2$ is a $C_1$ to $C_{20}$ hydrocarbon group, X is $R^2$ or a halogen atom, and $R^3$, $R^4$, $R^5$, and $R^6$ are each independently a hydrogen atom or a $C_1$ to $C_{10}$ alkyl group.

In another embodiment of the catalyst system, with regard to Formula 2, $R^2$ may be methyl or ethyl groups, X may be $R^2$ or a chlorine atom, $R^3$ and $R^6$ may be methyl groups, and $R^4$ and $R^5$ may be hydrogen atoms.

The catalyst systems according the aforementioned embodiments may further include a hydrocarbon solvent.

Another embodiment of the present invention relates to a method of polymerizing olefins, the method including a step of preparing an olefin polymer by bringing the catalyst system according to any one of the aforementioned embodiments into contact with a $C_2$ to $C_{10}$ olefin monomer.

The olefin monomer may be ethylene and the olefin polymer may be an olefin trimer.

Advantageous Effects

Embodiments of the present invention provide a chromium compound having a novel structure. In addition, the present invention provides a catalyst system, which allows a simple catalyst preparation process, exhibits superior catalytic activity upon an ethylene trimerization reaction, and includes the chromium compound, and a method of preparing 1-hexene using the catalyst system.

BEST MODE

Hereinafter, the present invention is described in detail.

Chromium Compound

All of a chromium compound represented by Formula 1a below, a chromium compound represented by Formula 1b below, and embodiments thereof are commonly designated as "chromium compounds," unless specified otherwise.

Embodiments of the present invention relates to a chromium compound having a novel structure represented by Formula 1a or 1b below:

[{CH$_3$(CH$_2$)$_3$CH(CH$_2$CH$_3$)CO$_2$}$_2$Cr(OH)], and  [Formula 1a]

[{CH$_3$CH$_2$CH(CH$_2$CH$_3$)CO$_2$}$_2$Cr(OH)].  [Formula 1b]

The chromium compound represented by Formula 1a is a trivalent chromium compound including two 2-ethyl hexanoate ({CH$_3$(CH$_2$)$_3$CH(CH$_2$CH$_3$)CO$_2$}) groups and one hydroxyl group (OH). When such a chromium compound is used in the catalyst system for polymerizing olefins, superior catalytic activity is exhibited in an ethylene trimerization reaction.

The chromium compound represented by Formula 1b is a trivalent chromium compound including two 2-ethylbutanoate ({CH$_3$CH$_2$CH(CH$_2$CH$_3$)CO$_2$}) groups and one hydroxyl group (OH). When such a chromium compound is used in the catalyst system for polymerizing olefins, superior catalytic activity is exhibited in an ethylene trimerization reaction.

In an embodiment, the chromium compound may include a compound represented by Formula 1c below:

[{CH$_3$(CH$_2$)$_3$CH(CH$_2$CH$_3$)CO$_2$}$_2$Cr(OH)]$_4$·2H$_2$O  [Formula 1c]

The chromium compound represented by Formula 1c has a structure wherein four trivalent chromium molecules having a structure of {CH$_3$(CH$_2$)$_3$CH(CH$_2$CH$_3$)CO$_2$}$_2$Cr(OH) are combined with two water molecule. Accordingly, when the chromium compound represented by Formula 1c is used in the catalyst system for polymerizing olefins, superior catalytic activity is exhibited in an ethylene trimerization reaction. The chromium compound represented by Formula 1c may be prepared from, for example, 2-ethylhexanoic acid, etc. through the aforementioned chromium compound preparation reaction. The 2-ethylhexanoic acid is cheap and industrially mass-produced. Accordingly, Formula 1c may be more economically prepared. In addition, since the chromium compound, etc. represented by Formula 1c has high solubility in aliphatic and aromatic hydrocarbon solvents, a catalyst may be more easily prepared. In addition, a catalyst system prepared using the chromium compound exhibits high catalytic activity.

The chromium compounds according to examples of the present invention may be prepared by reacting, for example, an aqueous solution of a trivalent chromium salt compound represented by Formula 6 below with an aqueous solution of a carboxylate alkali metal salt represented by Formula 7 below (hereinafter referred to as "reaction to prepare a chromium compound"):

Cr(X$^1$)$_3$  [Formula 6]

wherein Formula 6, X$^1$ is a halogen atom, a nitrate ion (NO$_3$), or a perchlorate ion (ClO$_4$). The halogen atom may be, for example, a chlorine atom (Cl), an iodine atom (I), a fluorine atom (F), a bromine atom (Br), or the like.

In particular, examples of the trivalent chromium salt compound represented by Formula 6 includes chromium chloride (CrCl$_3$) and a hydrate thereof (CrCl$_3$·H$_2$O), chromium nitrate (Cr(NO$_3$)$_3$) and a hydrate thereof (Cr(NO$_3$)$_3$·H$_2$O), chromium perchlorate (Cr(ClO$_4$)$_3$) and a hydrate thereof (Cr(ClO$_4$)$_3$·H$_2$O), and the like, but the present invention is not limited thereto. In an embodiment, when, as the trivalent chromium salt compound, a hydrate (for example, CrCl$_3$·H$_2$O, Cr(NO$_3$)$_3$·H$_2$O, Cr(ClO$_4$)$_3$·H$_2$O, or the like) is used, high solubility with respect to water is provided, whereby reactivity may be increased and economic efficiency may be provided.

(R$^1$CO$_2$)M  [Formula 7]

In Formula 7, M is an alkali metal. The alkali metal may be, for example, sodium (Na), potassium (K), lithium (Li), or the like. In Formula 7, R$^1$ is a C$_3$ to C$_{30}$ alkyl group or a C$_6$ to C$_{40}$ aryl group.

The alkali metal salt represented by Formula 7 may be easily obtained, for example, by reacting, a carboxylic acid (for example, 2-ethylhexanoic acid, 2-ethylbutyric acid, or the like) with an alkali metal hydroxide salt (NaOH, KOH, LiOH, or the like), in a predetermined equivalent ratio, in water.

In particular, the carboxylate alkali metal salt represented by Formula 7 below may be a compound represented by Formula 7a or 7b below:

{CH$_3$(CH$_2$)$_3$CH(CH$_2$CH$_3$)CO$_2$}M, and  [Formula 7a]

{CH$_3$CH$_2$CH(CH$_2$CH$_3$)CO$_2$}M.  [Formula 7b]

In Formulas 7a and 7b, M is an alkali metal. The alkali metal may be, for example, sodium (Na), potassium (K), lithium (Li), or the like.

More particularly, the carboxylate alkali metal salt represented by Formula 7a or 7b may be, for example, sodium 2-ethyl hexanoate, sodium 2-ethylbutanoate, or the like, but the present invention is not limited thereto. In an embodiment, when sodium 2-ethyl hexanoate or sodium 2-ethylbutanoate is used, the compound by represented Formula 1a, 1b or 1c may be advantageously prepared and a raw material may be easily obtained, thereby reducing the unit cost of production.

In reaction to prepare the chromium compound (reaction of an aqueous solution of a trivalent chromium salt compound with an aqueous solution of the carboxylate alkali metal salt), a reaction temperature may be 20° C. to 100° C., for example 50° C. to 100° C. Particularly, the temperature may be 80° C. to 95° C. In the reaction, an equivalent ratio of an alkali metal salt of a carboxylic acid (for example, 2-ethylhexanoic acid, 2-ethylbutanoic acid, or the like) to the trivalent chromium salt compound (1 equivalent) may be 1:3 to 1:4, particularly 1:3 to 1:3.5 or 1:3 to 1:3.2. Within the range, the chromium compound may be obtained in high yield.

When the reaction to prepare the chromium compound is performed within the temperature range and the equivalent ratio range, a chromium compound and a by-product, a carboxylic acid (for example, 2-ethylhexanoic acid, 2-ethylbutanoic acid, or the like), may be generated.

In the reaction to prepare the chromium compound, a hydrocarbon solvent (for example, methylcyclohexane, mineral spirits, etc.) may be further included. The chromium compound prepared by the reaction and 1 equivalent of a carboxylic acid (for example, 2-ethylhexanoic acid, 2-ethylbutanoic acid, or the like), as a by-product of the reaction, has low solubility with respect to water, but high solubility with respect to a hydrocarbon solvent. Accordingly, when, during the reaction to prepare a chromium compound, the hydrocarbon solvent is additionally added, the generated chromium compound and the by-product, carboxylic acid (for example, 2-ethylhexanoic acid, 2-ethylbutanoic acid, or the like), are dissolved in a layer of the hydrocarbon solvent and other by-products and unreactive products remain in an aqueous solution layer, whereby isolation and purification may be facilitated.

For example, when a hydrocarbon solvent is further added, a hydrocarbon solvent layer is collected after the chromium compound preparation reaction and then the collected hydrocarbon solvent layer is washed with an alkaline aqueous solution, whereby a by-product, a carboxylic acid (for example, 2-ethylhexanoic acid, 2-ethylbutanoic acid, or the like), may be extracted by an alkaline aqueous solution layer and thus removed. By such a method, a chromium compound may be easily obtained in solution with a hydrocarbon solvent. A resultant solution may be directly used to prepare the catalyst system. Alternatively, as needed, the resultant solution may be used in a powder form after removing a solvent therefrom through distillation.

The hydrocarbon solvent may be, for example, a $C_4$ to $C_{20}$ aliphatic hydrocarbon solvent, a $C_6$ to $C_{20}$ aromatic hydrocarbon solvent, a mixture thereof, or the like. In particular, the aliphatic hydrocarbon solvent may be, for example, isobutane, pentane, hexane, heptane, octane, nonane, decane, cyclohexane, methylcyclohexane, etc. and the aromatic hydrocarbon solvent may be, for example, benzene, toluene, xylene, mesitylene, ethylbenzene, cumene, etc.

The structure of the chromium compound prepared according to the method may be confirmed by analyzing elemental analysis data, observing O—H stretching signals at 3,630 $cm^{-1}$ of an IR spectrum, etc.

In addition, by measuring the mass of an obtained chromium compound, with respect to the mass of an added trivalent chromium salt compound, and the mass of 1 equivalent carboxylic acid (for example, 2-ethylhexanoic acid, 2-ethylbutanoic acid, or the like) generated as a by-product, the production of a chromium compound having the composition of Formula 1a, 1b or 1c may be additionally confirmed.

In addition, when the chromium compound is prepared using chromium chloride($CrCl_3$) as a trivalent chromium salt compound, the structure of the chromium compound may be additionally verified by titrating the amount of chlorine ions ($Cl^-$) remaining in an aqueous solution layer with silver nitrate ($AgNO_3$) or analyzing the acidity of the aqueous solution layer.

In an embodiment, when the acidity of an aqueous solution layer is analyzed and, as a result, is neutral in the case in which a chromium compound is prepared using chromium chloride ($CrCl_3$) as a trivalent chromium salt compound, it can be confirmed that the prepared chromium compound is composed of a composition including $\{CH_3CH_2CH(CH_2CH_3)CO_2\}_2Cr(OH)$, $\{CH_3(CH_2)_3CH(CH_2CH_3)CO_2\}_2Cr(OH)$ or $[\{CH_3(CH_2)_3CH(CH_2CH_3)CO_2\}_2Cr(OH)]_4 \cdot H_2O)$.

In addition, the shape and structure of the prepared chromium compound may be investigated from a molecular weight, which is calculated from freezing point depression measured in benzene, and elemental analysis data.

In an embodiment, the chromium compound represented by Formula 1c may have, more particularly, a structure represented by Formula 1d below:

[Formula 1d]

wherein IV is an ethylpentyl group ($CH_3(CH_2)_3CH(CH_2CH_3)$—). The chromium compound represented by Formula 1d has an adamantane structure.

A chromium compound having such an adamantane structure may be prepared according to, for example, the method of Example 5 described below. The presence of the chromium compound having the adamantane structure may be inferred from the structure of a cluster compound composed of four chromium atoms (FIG. 4), which is determined by analyzing the structure of a single crystal of an intermediate compound, which is partially precipitated by a catalyst solution prepared according to Example 5, using an X-ray diffraction method.

When the chromium compound represented by Formula 1c ($[\{CH_3(CH_2)_3CH(CH_2CH_3)CO_2\}_2Cr(OH)]_4 \cdot 2H_2O$) has an adamantane structure represented by Formula 1 d, the shape of the chromium compound may be stably maintained. In this case, a method of preparing the chromium compound is more reliable, thus being efficient and having economic feasibility. In addition, the chromium compound with the adamantane structure has high solubility and, when dissolved, low viscosity, thereby having superior handling property and superior uniformity in a reaction.

In addition, the structure of the compound represented by Formula 1c, i.e., $[\{CH_3(CH_2)_3CH(CH_2CH_3)CO_2\}_2Cr(OH)]_4 \cdot 2H_2O$, which has a shape wherein four $\{CH_3(CH_2)_3CH(CH_2CH_3)CO_2\}_2Cr(OH)$ molecules are combined with two water molecule, may be determined by molecular weight and elemental analysis data calculated from a value of freezing point depression measured in benzene.

Structural stability of the chromium compound represented by Formula 1 d including two water molecules may be determined by confirming that the water molecules are not removed from the chromium compound at all, when the chromium compound is dissolved in xylene to remove two water molecules coordinated therein and then refluxed at 160° C. for 10 hours by means of a Dean-Stark device. In addition, it was confirmed that molecular weights were not changed by calculating IR spectrum results, elemental analysis data, and measured values of freezing point depression in benzene, before and after the dehydration reaction. In the case of $Cr(EH)_3$ used in the preparation of conventional Philips catalysts, the composition of $Cr(EH)_3$ is different according to the batches of prepared compounds, and thus, there are problems regarding reliability and reproducibility. However, in the case of the chromium compound of Formula 1 d provided in the present invention, reproducibility and reliability may be easily secured, upon preparation of the chromium compound and the catalyst, due to a stable structure of the chromium compound.

In an embodiment, the aforementioned chromium compounds may be coordinated with a neutral ligand such as tetrahydrofuran, dimethylsulfoxide, or pyridine, but the present invention is not limited thereto. Such neutral ligands may be easily decoordinated by a Lewis acidic aluminum compound upon preparation of a catalyst system described below. In addition, when a chromium compound reacts with an aluminum compound described below, a carboxylate group of the chromium compound is exchanged with a hydrocarbon group ($R^2$—) of the aluminum compound, the carboxylate group may be released from the chromium compound.

Catalyst System Including Chromium Compound

Another embodiment of the present invention relates to a catalyst system including the aforementioned chromium compound. The catalyst system may include, in addition to the chromium compound, an aluminum compound and a pyrrole compound; or an aluminum compound and an alumino-pyrrole compound. When such a catalyst system is used in an olefin polymerization reaction, high activity is exhibited.

In an embodiment, the a catalyst system includes a reaction product of a chromium compound represented by Formula 1 below; an aluminum compound represented by Formula 3 below; and a pyrrole compound represented by Formula 4 below. Since such a catalyst system do not produce precipitates upon catalyst preparation, a filtration process is not required and thus a catalyst may be easily prepared. In addition, such a catalyst system is very useful in an ethylene trimerization reaction.

[Formula 1]

In Formula 1, $R^1$ is a $C_3$ to $C_{30}$ alkyl group or a $C_6$ to $C_{40}$ aryl group.

In particular, the alkyl group may be a $C_3$ to $C_{10}$ linear, branched, or cyclic alkyl group. More particularly, the alkyl group may be a $C_5$ to $C_7$ branched alkyl group. In particular, the aryl group may be a $C_6$ to $C_{12}$ aryl group.

for example, $R^1$ may be an n-propyl group, an isopropyl group, an n-butyl group, an isobutyl group, a sec-butyl group, an n-pentyl group, an isopentyl group, a neopentyl group, a 1,2-dimethylpropyl group, an n-hexyl group, a cyclohexyl group, a 1,3-dimethylbutyl group, a 1-isopropylpropyl group, a 1-ethylpropyl group, a 1,2-dimethylbutyl group, an n-heptyl group, a 1,4-dimethylpentyl group, a 2-methyl-1-isopropylpropyl group, a 1-ethyl-3-methylbutyl group, a 1-ethylpentyl group, an n-octyl group, a 2-ethylhexyl group, a 3-methyl-1-isopropylbutyl group, a 2-methyl-1-isopropylbutyl group, a phenyl group, a naphthyl group, or the like, but the present invention is not limited thereto.

In an embodiment, the chromium compound represented by Formula 1 may include particularly one or more of compounds represented by Formula 1a or 1b below:

[Formula 1a]

[Formula 1b]

In an embodiment, the chromium compound includes a compound represented by Formula 1c below.

[Formula 1c]

In an embodiment of the catalyst system, the aluminum compound is a compound represented by Formula 3 below:

[Formula 3]

wherein $R^2$ is a $C_1$ to $C_{20}$ hydrocarbon group, $X^2$ is a halogen atom, and an average value of n is 1 to 3.

The hydrocarbon group may be, particularly, a $C_1$ to $C_{20}$ alkyl group, a $C_1$ to $C_{15}$ alkyl group, a $C_1$ to $C_{10}$ alkyl group, or a $C_1$ to $C_5$ alkyl group. The alkyl group may have, for example, a linear, branched, or cyclic structure. More particularly, the hydrocarbon group may be, for example, a methyl group, an ethyl group, a propyl group, an isobutyl group, or the like.

The halogen atom may be, for example, a chlorine atom (Cl), an iodine atom (I), a fluorine atom (F), a bromine atom (Br) and n may be, for example, 2 to 3.

In an embodiment, the aluminum compound may be a single compound or a mixture of aluminum compounds, n values of which are different, but the present invention is not limited thereto. In particular, the aluminum compound may be an aluminum compound (($R^2)_3Al$) represented by Formula 3, wherein n is 3, and/or an aluminum compound (($R^2)_2Al(X^2)$) represented by Formula 3, wherein n is 2. Among these, triethylaluminum ($Et_3Al$) and diethylaluminumchloride ($Et_2AlCl$) represented by Formula 3, wherein $R^2$ is an ethyl group, are massively used as a promoter of a Ziegler-Natta catalyst in the industry and are cheap, thereby being used to increase economic efficiency. But the present invention is not limited thereto. The $(R^2)_2Al(X^2)$ may be obtained by reacting $(R^2)_3Al$ with various organic and inorganic substances including a halogen.

In addition, a mix ratio (molar ratio) of $(R^2)_3Al:(R^2)_2Al(X^2)$ may be 1:0.5 to 1:2, for example, 1:1, but the present invention is not limited thereto.

In an embodiment of the catalyst system, the aluminum compound represented by Formula 3 may be a mixture of triethylaluminum ($Et_3Al$) and diethylaluminumchloride ($Et_2AlCl$). In this case, a mix ratio (molar ratio) of triethylaluminum ($Et_3Al$):diethylaluminumchloride ($Et_2AlCl$) may be 1:0.5 to 1:2, for example, 1:1. Within this range, reaction efficiency of the catalyst system may be increased without an excessive remainder of an unreacted aluminum compound.

A molar ratio of the chromium compound to the aluminum compound (Cr:Al), which are added upon preparation (reaction) of the catalyst system, may be 1:3 to 1:100, for example, 1:10 to 1:50, particularly 1:10 to 1:40. Within this range, a highly active catalyst system may be realized while increasing economic efficiency. In this case, 1-hexene, as an ethylene trimer, may be obtained in high yield and in high purity.

In the catalyst system, the aluminum compound may participate in a reaction of forming an active catalyst species by reacting with the chromium compound and the pyrrole compound. In addition, a portion of the aluminum compound may remove a catalytic poison, such as water or oxygen included in a solvent and a monomer, upon catalyst system preparation or olefin polymerization (trimerization). Since the amounts of water, oxygen, etc. included in a solvent and a monomer may differ on a case-by-case basis, an optimal addition amount of the aluminum compound may be differently set according to each case.

In addition, when the catalyst system is used in olefin polymerization, an aluminum compound may be separately added to an olefin polymerization reaction solvent, regardless of the catalyst system, to remove water, oxygen, etc. In this case, the amount of the aluminum compound separately added to the olefin polymerization reaction solvent is not included in the molar ratio.

In an embodiment of the catalyst system, a pyrrole compound reacting with the chromium compound represented by Formula 1 or the aluminum compound represented by Formula 3 may be a compound represented by Formula 4 below:

[Formula 4]

wherein $R^3$, $R^4$, $R^5$, and $R^6$ are each independently a hydrogen atom or a $C_1$ to $C_{10}$ alkyl group.

In Formula 4, the alkyl group may have, for example, a carbon number of 1 to 8, 1 to 6, or 1 to 4 and a linear, branched, or cyclic structure. In particular, the alkyl group may be, for example, a methyl group, an ethyl group, a propyl group, an isobutyl group, or the like.

More particularly, the pyrrole compound represented by Formula 4 may be, for example, a pyrrole ($R^3$, $R^4$, $R^5$, and $R^6$ of Formula 4 are hydrogen atoms), a pyrrole compound (Formula 4, $R^3$ is a hydrogen atom and one or more of $R^4$, $R^5$, and $R^6$ is a $C_1$ to $C_{10}$ alkyl group), or the like, but the present invention is not limited thereto.

In an embodiment of the catalyst system, the pyrrole compound represented by Formula 4 may be 2,5-dimethylpyrrole wherein $R^3$ and $R^6$ of Formula 4 are methyl groups. In this case, the cost of a raw material is low and a highly active catalyst system may be realized.

In the catalyst system, a molar ratio of the chromium compound to the pyrrole compound (chromium compound: pyrrole compound) added upon preparation (reaction) may be 1:1 to 1:10, for example, 1:1 to 1:5. Particularly, the molar ratio may be 1:1 to 1:3. Within this range, the catalyst system exhibits superior activity, thereby obtaining highly pure 1-hexene, as an ethylene trimer, in high yield.

In an embodiment, an alumino-pyrrole compound represented by Formula 5 described below may be prepared by reacting the chromium compound represented by Formula 1, the aluminum compound represented by Formula 3, and the pyrrole compound represented by Formula 4 in a hydrocarbon solvent, through the catalyst system.

In another embodiment, the alumino-pyrrole compound represented by Formula 5 described below may be prepared, through the catalyst system, by preparing a mixture including the aluminum compound represented by Formula 3 and the pyrrole compound represented by Formula 4 and then reacting the mixture with the chromium compound in a hydrocarbon solvent.

In another embodiment, the catalyst system includes a reaction product of the chromium compound represented by Formula 1c; the aluminum compound represented by Formula 3; and the alumino-pyrrole compound represented by Formula 5 described below. Such a catalyst system is very useful in an ethylene trimerization reaction. In addition, such a catalyst system allows preparation of a catalyst in an aliphatic hydrocarbon solvent, thus being more useful.

The chromium compound represented by Formula 1c and the aluminum compound represented by Formula 3 are described in the aforementioned embodiments.

[Formula 5]

In Formula 5, $R^2$ is a $C_1$ to $C_{20}$ hydrocarbon group and $R^3$, $R^4$, $R^5$, and $R^6$ are each independently a hydrogen atom or a $C_1$ to $C_{10}$ alkyl group.

In Formula 5, $R^2$ may be, particularly, a hydrocarbon group, for example, a $C_1$ to $C_{20}$ alkyl group, a $C_1$ to $C_{15}$ alkyl group, or a $C_1$ to $C_{10}$ or a $C_1$ to $C_5$ alkyl group.

In Formula 5, $R^3$, $R^4$, $R^5$, and $R^6$ are each independently a hydrogen atom or, for example, a $C_1$ to $C_8$, a $C_1$ to $C_6$, or a $C_1$ to $C_4$ alkyl group.

In Formula 5, the alkyl group may have a linear, branched, or cyclic structure. More particularly, the alkyl group may be, for example, a methyl group, an ethyl group, a propyl group, an isobutyl group, or the like.

In the alumino-pyrrole compound represented by Formula 5 of an embodiment of the catalyst system, $R^3$ and $R^6$ may be methyl groups, $R^4$ and $R^5$ may be hydrogen, and $R^2$ may be an ethyl group. When such an alumino-pyrrole compound is used, the catalyst system exhibits high activity.

In an embodiment, the alumino-pyrrole compound may be prepared by a method of reacting, for example, the pyrrole compound represented by Formula 4 with $(R^2)_3Al$; or a method of forming the pyrrole compound represented by Formula 4 into an N-lithio-pyrrole compound using n-BuLi, etc. and then reacting the N-lithio-pyrrole compound with $(R^2)_2AlCl$. Here, the reaction solvent may be diethyl ether, or the like. In this case, aluminum of the compound represented by Formula 5 may be coordinated with diethyl ether. Since diethyl ether coordinated with aluminum is easily decoordinated upon the preparation of the catalyst system, the presence or absence of the coordinated diethyl ether does not greatly affect the activity of the prepared catalyst system.

In an embodiment, a molar ratio of the chromium compound to the alumino-pyrrole compound (chromium compound:alumino-pyrrole compound) may be 1:1 to 1:10, for example 1:1 to 1:5. Particularly, the molar ratio may be 1:1 to 1:3. Within this range, the catalyst system exhibits superior activity and high-purity 1-hexene, as an ethylene trimer, may be obtained in high yield.

In an embodiment, the catalyst system may be prepared (reacted) at −30 to 50° C., for example 0 to 40° C. Particularly, the catalyst system may be prepared at 15 to 35° C. Within this range, the catalyst system may be obtained in high yield.

According to the embodiments, the catalyst system may further include a hydrocarbon solvent. When the hydrocarbon solvent is included, the reaction product of the catalyst system may be present as a uniform solution dissolved in the hydrocarbon solvent.

In addition, the catalyst system manufactured by Philips, as described in the Background Art, essentially requires an aromatic hydrocarbon solvent. However, the catalyst system according to the embodiments of the present invention has superior solubility with respect to a hydrocarbon solvent and exhibits high activity in an aliphatic hydrocarbon solvent. Accordingly, the catalyst system may be prepared in an aliphatic hydrocarbon solvent during the ethylene trimerization reaction, whereby an aromatic hydrocarbon solvent removal process and a filtration process may be omitted.

The hydrocarbon solvent may be, for example, a $C_4$ to $C_{20}$ aliphatic hydrocarbon solvent, a $C_6$ to $C_{20}$ aromatic hydrocarbon solvent, a mixture thereof, or the like. The aliphatic hydrocarbon solvent may be, for example, isobutane, pentane, hexane, heptane, octane, nonane, decane, cyclohexane, methylcyclohexane, or the like. Particular examples of the aromatic hydrocarbon solvent include benzene, toluene, xylene, mesitylene, ethylbenzene, cumene, and the like. The ethylene trimerization reaction is carried out in an aliphatic hydrocarbon solvent. Accordingly, when the same aliphatic hydrocarbon solvent as the solvent used in the ethylene trimerization reaction is used to prepare the catalyst system, isolation and purification processes, after the reaction, may be easily performed.

The aforementioned embodiment of the catalyst system may be obtained by, for example, contacting the chromium compound represented by Formula 1, the aluminum compound represented by Formula 3, and a pyrrole compound represented by Formula 4 below in a hydrocarbon solvent and reacting the same. In particular, the embodiment of the catalyst system may be prepared by adding the aluminum compound to a mixture prepared by adding the chromium compound and the pyrrole compound in the hydrocarbon solvent and reacting the same.

The aforementioned another embodiment of the catalyst system may be obtained by, for example, reacting the chromium compound represented by Formula 1c, the aluminum compound represented by Formula 3, and an alumino-pyrrole compound represented by Formula 5 below in a hydrocarbon solvent.

In another embodiment, the catalyst system may include a mixture of a catalyst precursor represented by Formula 2 below; and an aluminum compound represented by Formula 3.

In the catalyst system, the catalyst precursor may be a compound represented by Formula 2 below:

[Formula 2]

In Formula 2, $R^2$ is a $C_1$ to $C_{20}$ hydrocarbon group and $R^3$, $R^4$, $R^5$, and $R^6$ are each independently a hydrogen atom or a $C_1$ to $C_{10}$ alkyl group.

In Formula 2, $R^2$ may be, particularly, a hydrocarbon group, for example, a $C_1$ to $C_{20}$ alkyl group, a $C_1$ to $C_{15}$ alkyl group, or a $C_1$ to $C_{10}$ or a $C_1$ to $C_5$ alkyl group.

In Formula 2, $R^3$, $R^4$, $R^5$, and $R^6$ are each independently a hydrogen atom or, for example, a $C_1$ to $C_8$, a $C_1$ to $C_6$, or a $C_1$ to $C_4$ alkyl group.

In Formula 2, the alkyl group may have a linear, branched, or cyclic structure. More particularly, the alkyl group may be, for example, a methyl group, an ethyl group, a propyl group, an isobutyl group, or the like.

In the catalyst precursor represented by Formula 2 of an embodiment of the catalyst system, $R^2$ may be a methyl group or an ethyl group, X may be the same as $R^2$ or a chlorine atom, $R^3$ and $R^6$ may be methyl groups, and $R^4$ and $R^5$ may be hydrogen atoms. When such a catalyst precursor is used, the catalyst system exhibits high activity.

In another embodiment of the catalyst system, the aluminum compound is the same as the aluminum compound represented by Formula 3 described in the aforementioned embodiments.

In an embodiment of the catalyst system, a molar ratio of the catalyst precursor represented by Formula 2 to the aluminum compound represented by Formula 3 (Cr:Al) may be 1:3 to 1:100, for example 1:10 to 1:50, 1:10 to 1:40, 1:10 to 1:30 or 1:10 to 1:20. Within this range, a highly active catalyst system may be realized while increasing economic efficiency. In this case, high-purity 1-hexene, as an ethylene trimer, may be obtained in high yield. In addition, the amount of an unreacted reaction product is decreased and thus the efficiency of the catalyst system may be further increased.

An embodiment of the catalyst system includes a mixture of the catalyst precursor represented by Formula 2 below and the aluminum compound represented by Formula 3. The mixture may be produced during, for example, a reaction process of the catalyst system according to the aforementioned embodiment or the catalyst system according to another embodiment.

Catalyst Precursor

Another embodiment of the present invention relates to the catalyst precursor represented by Formula 2. Such a catalyst precursor may be derived from the chromium compound represented by Formula 1. Detailed description for the catalyst precursor is the same as that for the aforementioned catalyst system.

In an embodiment, the catalyst precursor may be obtained by, for example, a preparation method using reaction in the catalyst system according to the aforementioned embodiments; a preparation method using a reaction of the chromium compound represented by Formula 1 with the compound represented by Formula 5; or the like, but the present invention is not limited thereto. For example, the catalyst precursor may be synthesized as described in Preparation Example 6 or 7 below.

Method of Polymerizing Olefins

Another embodiment of the present invention relates to a method of polymerizing olefins using the aforementioned catalyst system.

The method includes a step of preparing an olefin polymer (trimer) by bringing the catalyst system into contact with a $C_2$ to $C_{10}$ olefin monomer.

The catalyst system of the present invention may be present in, as well as a uniform solution, a carrier-included form, an insoluble particle form in a carrier, or the like.

Accordingly, the olefin polymerization (trimerization) may be a liquid-phase, slurry-phase, bulk-phase, or gas-phase polymerization reaction. In addition, each polymerization reaction condition may be variously modified according to the states of used catalysts (uniform or non-uniform state (supported type)), polymerization methods (solution polymerization, slurry polymerization, and gas phase polymerization), desired polymerization results, or polymer types. Such modifications may be easily made by those skilled in the art. When the polymerization is performed in a liquid or slurry phase, a hydrocarbon solvent or an olefin monomer itself may be used as a medium. The hydrocarbon solvent may be a $C_4$ to $C_{20}$ aliphatic hydrocarbon solvent, a $C_6$ to $C_{20}$ aromatic hydrocarbon solvent, a mixture thereof, or the like. The aliphatic hydrocarbon solvent may be, for example, isobutane, pentane, hexane, heptane, octane, nonane, decane, cyclohexane, methylcyclohexane, or the like. Particular examples of the aromatic hydrocarbon solvent include benzene, toluene, xylene, mesitylene, ethylbenzene, cumene, and the like. In general, the olefin polymerization (trimerization) reaction may be carried out in an aliphatic hydrocarbon solvent considering environmental problems. In addition, when isolation from an olefin polymer, as a product produced after reaction, is considered, a difference between the boiling point of a used hydrocarbon solvent and the boiling point of the product is preferably 10 to 50° C. For example, when the olefin monomer is ethylene and the product is 1-hexene (boiling point: 63° C.), production costs are low and cyclohexane having a boiling point of 80.74° C. or methylcyclohexane having a boiling point of 101° C. may be used.

In an embodiment, examples of the olefin monomer include ethylene, propylene, 1-butene, 1-hexene, 1-octene, 1-decene, a mixture thereof, and the like. Preferably, ethylene is used alone.

In the olefin polymerization (trimerization) method of the present invention, a use amount of the catalyst system is not specifically limited. However, since the catalyst system of the present invention exhibits high activity, the catalyst system may be used in a small amount, compared to conventional catalyst systems, to cause a reaction. In an embodiment, the olefin polymerization method is solution polymerization, the catalyst system is added at a molar concentration (based on chromium) of 0.01 mmol/L to 0.1 mmol/L, for example, 0.01 mmol/L to 0.03 mmol/L, with respect to the hydrocarbon solvent, and then reaction is performed for thirty minutes to one hour by continuously adding an olefin monomer, such as ethylene. Accordingly, the volume of a resultant solution may be about two times an initial volume due to the generated olefin polymer (trimer), such as 1-hexene. For reference, in the case of a published patent document of Philips, catalytic activity is lower than that of the catalyst system of the present invention and thus a polymerization reaction is performed at a catalyst concentration of about 0.25 mmol/L (see U.S. Pat. No. 5,856,257).

In addition, upon the olefin polymerization (trimerization) of the present invention, a temperature may be changed according to reaction substances, reaction conditions, and the like. The temperature may be 0° C. to 150° C., for example, 60° C. to 130° C. For example, the polymerization may be performed in a batch, semi-continuous, or continuous process. The polymerization may be carried out through two or more steps, reaction conditions of which are different.

Hereinafter, the constitution and functions of the present invention are described in more detail with reference to examples of the present invention. However, the following examples are merely provided as preferred embodiments and, therefore, the present invention is not limited to the examples.

EXAMPLE

Preparation Example 1: Preparation of Chromium Compound Represented by Formula 1a 2-ethylhexanoic acid (2.44 g, 16.9 mmol) was fed into a 1-neck flask, and then NaOH (0.68 g, 16.9 mmol) dissolved in distilled water (13 ml) was added thereto, thereby preparing sodium 2-ethyl hexanoate.

Subsequently, mineral spirits (5 ml) were additionally added thereto to form two phases. While stirring the resultant mixture at 95° C., hydrated chromium (III) chloride ($CrCl_3 \cdot H_2O$, 1.50 g, 96%, 5.40 mmol) dissolved in distilled water (1 ml) was slowly added thereto. A reaction was rapidly performed and a product was dissolved into an organic layer. After allowing reaction for 2 hours, an aqueous layer became transparent and all of generated products were dissolved into an organic layer. Accordingly, the organic layer appeared navy blue.

The aqueous solution layer collected after the two-phase reaction was almost neutral. In addition, after the two-phase reaction, silver nitrate ($AgNO_3$) was added to the aqueous solution layer and thus the mass of precipitated silver chloride (AgCl) was measured. The mass of precipitated silver chloride (AgCl) was 2.28 g. From this data, it can be confirmed that Cl ions of added $CrCl_3$ are almost completely removed (calculated value: 2.32 g).

Only the organic layer was collected, washed with distilled water (10 ml) twice, and subjected to vacuum distillation (0.3 mmHg, 130° C.), thereby removing the mineral spirits and by-products, 2-ethylhexanoic acid and remaining moisture. As a result, 1.94 g of a navy blue solid-type chromium compound represented by Formula 1a was obtained (yield: 101%). An aqueous NaOH solution was added to a mixture of 2-ethylhexanoic acid and mineral spirits outflowed during the vacuum distillation and thus sodium 2-ethyl hexanoate was formed. The formed sodium 2-ethyl hexanoate was extracted into an aqueous solution layer and then hydrochloric acid was added to the aqueous solution layer at the same time. Reproduced 2-ethylhexanoic acid was extracted with diethyl ether and the mass thereof was measured. The measured mass was 0.80 g. From this result, it was confirmed that 1.0 equivalent (calculated value: 0.78 g) of 2-ethylhexanoic acid with respect to the added trivalent chromium salt compound was produced as a by-product {Anal. calc. ($C_{16}H_{31}CrO_5$): C, 54.07; H, 8.79; Found: C, 54.67; H, 9.03}.

The chromium compound obtained according to Preparation Example 1 was subjected to IR spectrum analysis. As a result, an O—H stretching signal was observed at 3630 $cm^{-1}$.

Preparation Example 2: Preparation of Chromium Compound Represented by Formula 1b A navy blue solid-type chromium compound represented by Formula 1b was prepared in the same manner as in Preparation Example 1, except that 2-ethylbutyric acid (16.9 mmol) was used instead of 2-ethylhexanoic acid (C, 48.52; and H, 7.85, and, with respect to {$CH_3CH_2CH(CH_2CH_3)CO_2$}$_2$Cr(OH), C, 48.15; and H, 7.75).

The compound prepared according to Preparation Example 2 was dissolved in benzene and then the molecular weight thereof was measured using a freezing point depression method. As a result, the molecular weight was 3330 and about 11 {CH$_3$CH$_2$CH(CH$_2$CH$_3$)CO$_2$}$_2$Cr(OH) molecules was present in benzene as an assembly (i.e., [{CH$_3$CH$_2$CH(CH$_2$CH$_3$)CO$_2$}$_2$Cr(OH)]$_{11}$).

As an elemental analysis result, the structure of the compound prepared according to Preparation Example 2 was identical to that of CH$_3$CH$_2$CH(CH$_2$CH$_3$)CO$_2$}$_2$Cr(OH), not including a water molecule.

When the compound prepared according to the Preparation Example 2 was dissolved in xylene and then refluxed at 160° C. for 10 hours, the color of the compound changed from navy blue to green and elemental analysis data values were also changed (C, 50.85; H, 7.96).

Preparation Example 3: Preparation of Chromium Compound Represented by Formula 1c 2-ethylhexanoic acid (2.44 g, 16.9 mmol) was fed into a 1-neck flask, and then NaOH (0.68 g, 16.9 mmol) dissolved in distilled water (13 ml) was added thereto, thereby preparing sodium 2-ethyl hexanoate. Subsequently, methylcyclohexane (7 ml) was additionally added thereto to form two phases. While stirring the resultant mixture at 95° C., hydrated chromium (III) chloride (CrCl$_3$.H$_2$O, 1.50 g, 96%, 5.40 mmol) dissolved in distilled water (1 ml) was slowly added thereto. A reaction was rapidly performed and a product was dissolved into an organic layer. After allowing reaction for 2 hours, an aqueous layer became transparent and all of generated products were dissolved into an organic layer. Accordingly, the organic layer appeared viscous navy blue and an aqueous layer became transparent.

The pH of the aqueous layer was neutral. In addition, it could be confirmed that, when considering that the weight of precipitated silver chloride (AgCl) was 2.28 g upon addition of a large amount of silver nitrate (AgNO$_3$, 3.03 g, 17.8 mmol), almost all of Cl ions of CrCl$_3$ were removed (calculated value: 2.32 g).

The organic layer was diluted by additionally adding hexane (5 ml). Subsequently, only the organic layer was collected and NaOH (0.22 g, 5.40 mmol) dissolved in distilled water (3 ml) was added thereto, followed by strongly stirring for 30 minutes. 2-ethylhexanoic acid (1 equivalent with respect to trivalent chromium salt compound) produced as a by-product and in a sodium salt form in an aqueous layer was removed. The organic layer was only collected and water remaining therein was removed with magnesium sulfate, followed by removing an organic solvent therefrom by vacuum drying (0.3 mmHg) at room temperature. As a result, a navy blue solid-type chromium compound ([{CH$_3$(CH$_2$)$_3$CH(CH$_2$CH$_3$)CO$_2$}$_2$Cr(OH)]$_4$.2H$_2$O) was obtained in an amount of 1.94 g. When calculated based on the structure of [{CH$_3$(CH$_2$)$_3$CH(CH$_2$CH$_3$)CO$_2$}$_2$Cr(OH)]$_4$.2H$_2$O, yield was 98%.

Figure 1:
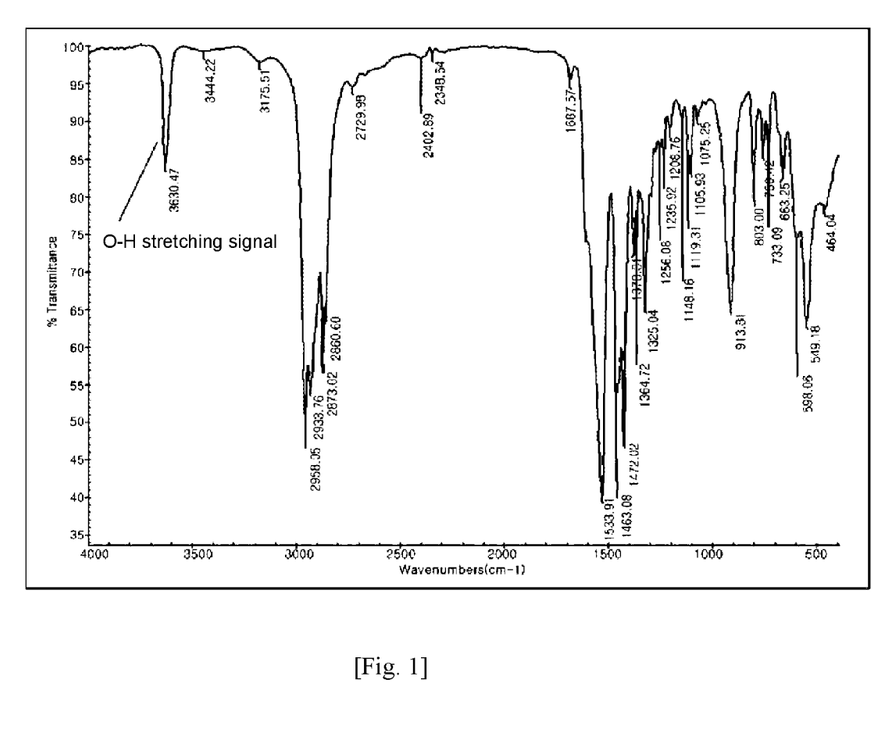
FIG. 1 illustrates the IR spectrum of a chromium compound prepared according to Preparation Example 3 of the present invention.

The IR spectrum of the prepared chromium compound is illustrated in FIG. 1. As a result of the IR spectrum analysis, it can be confirmed that an O—H stretching signal is observed at 3630 cm$^{-1}$. After dissolving the chromium compound in benzene, the molecular weight thereof was measured using a freezing point depression method. As a result, the molecular weight was 1580 which is close to the molecular weight of the tetramer. In addition, as an elemental analysis result, the structure of chromium compound was identical to that of [{CH$_3$(CH$_2$)$_3$CH(CH$_2$CH$_3$)CO$_2$}$_2$Cr(OH)]$_4$.2H$_2$O (C, 52.48; and H, 8.88, and, a calculated theoretical value of [{CH$_3$(CH$_2$)$_3$CH(CH$_2$CH$_3$)CO$_2$}$_2$Cr(OH)]$_4$.2H$_2$O, C, 52.73; and H, 8.85).

When the chromium compound prepared according to Preparation Example 3 was dissolved in xylene and then refluxed at 160° C. for 10 hours, navy blue was maintained with little color change. In addition, it was confirmed that elemental analysis data values hardly changed and thus a stable shape was maintained.

Preparation Example 4: Preparation of Alumino-Pyrrole Compound (B1)

Under an inert atmosphere (nitrogen), triethylaluminum (7.20 g, 63.1 mmol) dissolved in toluene (60 ml) was fed into a 1-neck flask, and then 2,5-dimethylpyrrole (1.50 g, 15.8 mmol) was additionally added thereto, followed by stirring at room temperature for five hours. Next, toluene and unreacted triethylaluminum were removed therefrom by vacuum distillation (0.3 mmHg, 70° C.), thereby obtaining 2.80 g of a pyrrole aluminum compound (1-(diethylalumino)-2,5-dimethylpyrrole) in which N—Al covalent bonds were formed. According to this method, an alumino-pyrrole compound (B1) which had the structure represented by Formula 5 in which R$^2$ was an ethyl group, R$^3$ and R$^6$ were methyl groups, R$^4$ and R$^5$ were hydrogen was prepared. A result of $^1$H NMR analysis is as follows: yield: 99%, $^1$H NMR (C$_6$D$_6$): a 5.51 (s, 2H, Ar—H), 2.01 (s, 6H, CH$_3$), 1.35 (t, J=8 Hz, 6H, CH$_3$), 0.35 (q, J=8 Hz, 4H, CH$_2$) ppm}.

Preparation Example 5: Preparation of Alumino-Pyrrole Compound (B2)

Under an inert atmosphere (nitrogen), 2,5-dimethylpyrrole (3.00 g, 31.5 mmol) was dissolved in diethyl ether (30 ml) in a 1-neck flask and a resultant solution was cooled to −78° C. Subsequently, n-butyllithium (13.7 g, 31.5 mmol, 1.6 M hexane solution) was slowly added thereto. After stirring overnight at room temperature, the mixture was re-cooled to −78° C. and then dimethylaluminumchloride (Me$_2$AlCl, 20.6 g, 31.5 mmol, 1.0 M hexane solution) was slowly added thereto. After stirring overnight, filtration was performed and, as a result, a yellow solution was obtained. Subsequently, the solution was subjected to vacuum drying, thereby obtaining 6.67 g of a (1-(dimethylalumino)-2,5-dimethylpyrrole) compound. According to this method, an alumino-pyrrole compound (B2) which had the structure represented by Formula 5 and in which R$^2$, R$^3$ and R$^6$ were methyl groups and R$^4$ and R$^5$ were hydrogen was prepared. As a result of $^1$H NMR analysis, it was confirmed that 1 equivalent of diethyl ether was attached to the alumino-pyrrole compound (B2) (yield: 94%). $^1$H NMR (C$_6$D$_6$): ä 6.23 (s, 2H, CH), 3.15 (q, J=7.2 Hz, 4H, CH$_2$), 2.44 (s, 6H, CH$_3$), 0.55 (t, J=6.8 Hz, 6H, CH$_3$), −0.33 (s, 6H, CH$_3$) ppm}.

Preparation Example 6: Preparation of Catalyst Precursor (P1)

Under an inert atmosphere (nitrogen), the chromium compound (Formula 1c, 200 mg, 0.563 mmol) prepared according to Preparation Example 3 dissolved in pentane (9.0 ml) was fed into a 25 ml 1-neck flask, and then the alumino-pyrrole compound (B2, 380 mg, 1.69 mmol) of Preparation Example 5 dissolved in toluene (1.0 ml) was slowly added thereto, such that two solution layers were formed. According to this method, a catalyst precursor (P1) which had the structure represented by Formula 2 and in which R$^2$, X, R$^3$ and R$^6$ were methyl groups and R$^4$ and R$^5$ were hydrogen was prepared.

Figure 2:
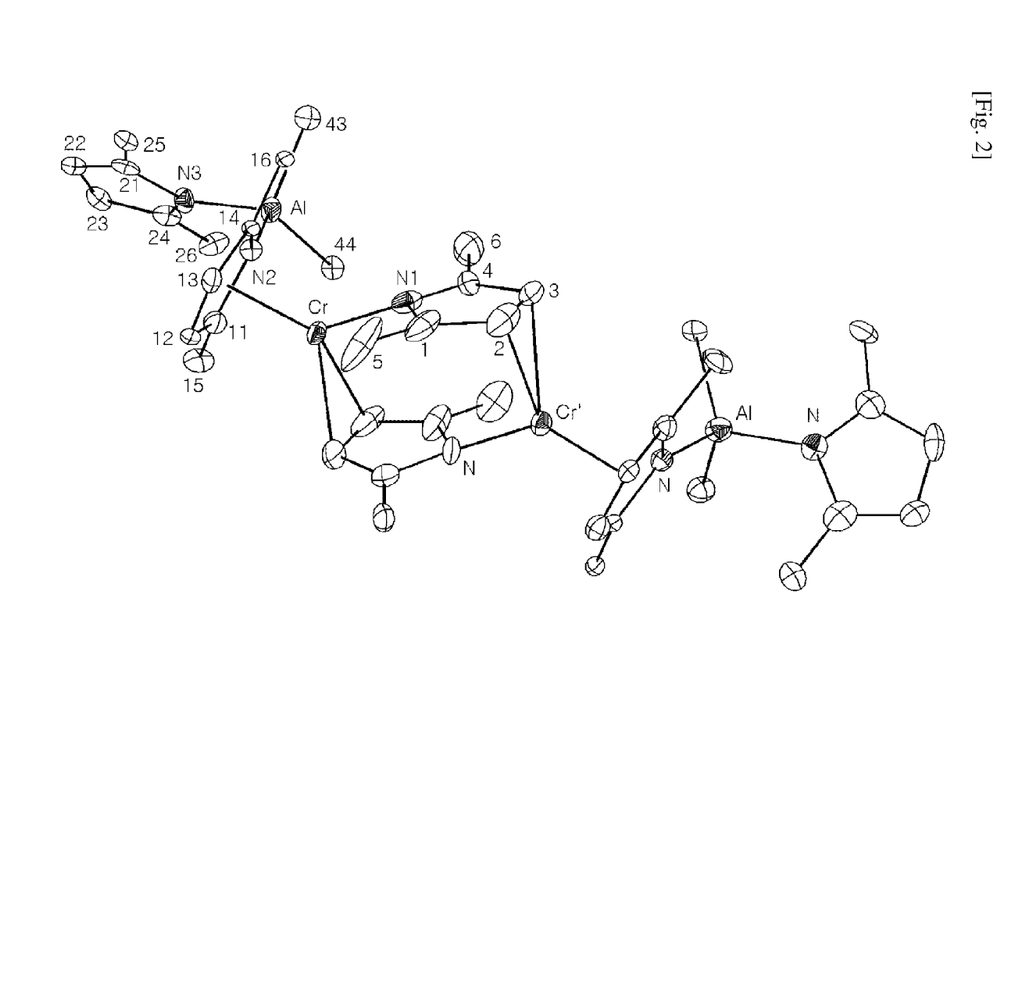
FIG. 2 illustrates the structure of a catalyst precursor (P1) prepared according to Preparation Example 6 of the present invention, investigated by single-crystal X-ray diffraction analysis.

In the state in which two solution layers were formed as described above, crystals were precipitated while allowing slow reaction for one week (143 mg, yield: 65%). The structure of an obtained single crystal was analyzed by an X-ray diffraction method. A result is illustrated in FIG. 2.

Preparation Example 7: Preparation of Catalyst Precursor (P2)

Under an inert atmosphere (nitrogen), lithium diisopropylamide (LiNiPr$_2$, 1.50 g, 14.0 mmol) dissolved in toluene (15 ml) was fed into a 1-neck flask, and then diethylaluminum chloride (Et$_2$AlCl, 0.844 g, 7.00 mmol) was added thereto at room temperature slowly, thereby preparing a mixture. After stirring for six hours at room temperature, generated lithium chloride was filtered out. Subsequently, an obtained solution was subjected to vacuum drying, thereby obtaining 1.64 g of LiAlEt$_2$(NiPr$_2$)$_2$ as a white solid {yield: 80%, $^1$H NMR (C$_6$D$_6$): ä 3.14 (m, 4H, CH), 1.56 (t, J=8.0 Hz, 6H, CH$_3$), 1.01 (d, J=6.4 Hz, 24H, CH$_3$), 0.34 (q, J=7.6 Hz, 4H, CH$_2$) ppm. $^{13}$C NMR (C$_6$D$_6$): ä 46.06, 26.25, 11.11, –8.18 ppm}. LiAlEt$_2$(NiPr$_2$)$_2$ (1.00 g, 3.42 mmol) was dissolved in toluene (15 ml) and then cooled to –30° C., followed by adding CrCl$_3$(THF)$_3$ (1.28 g, 3.42 mmol) thereto. During stirring for eight hours at room temperature, the color of the solution changed from dark green to blue. A solvent was removed from the solution by means of a vacuum pump and then hexane (20 ml) was added thereto. Precipitated lithium chloride was removed through filtration and cooling to –30° C. was performed, thereby obtaining crystals (770 mg). Crystals (100 mg, 0.245 mmol) obtained according to the method were dissolved in toluene (1 ml), and then the compound (132 mg, 0.735 mmol) represented by Formula 5, which was prepared according to Preparation Example 4, dissolved in toluene (1 ml) was added thereto at room temperature.

According to this method, a catalyst precursor (P2) which had the structure represented by Formula 2 and in which R$^2$ was an ethyl group, X was a chlorine atom, R$^3$ and R$^6$ were methyl groups, and R$^4$ and R$^5$ were hydrogen was prepared.

Figure 3:
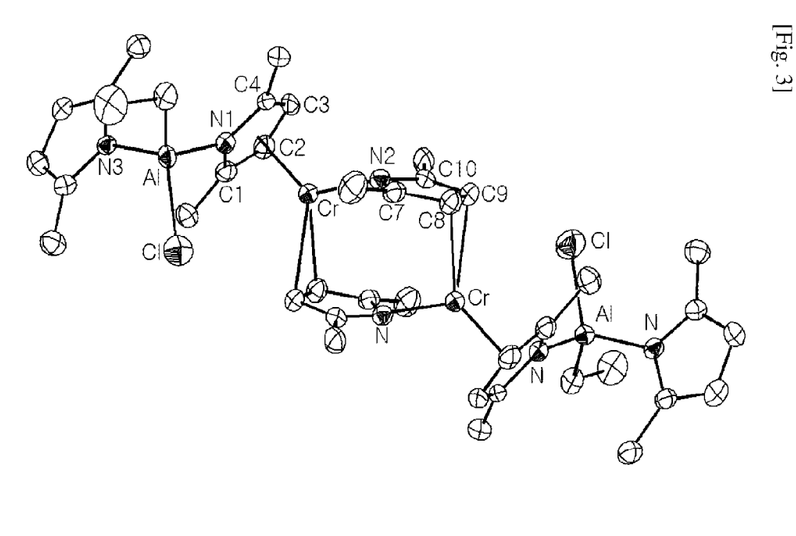
FIG. 3 illustrates the structure of a catalyst precursor (P2) prepared according to Preparation Example 7 of the present invention, investigated by single-crystal X-ray diffraction analysis.

A resultant reaction solution was stirred for one hour, and then diffused with pentane overnight, thereby decreasing solubility and thus precipitating crystals (90 mg). An obtained single crystal compound was subjected to an X-ray diffraction analysis. An analyzed structure is illustrated in FIG. 3.

Hereinafter, the following examples and comparative examples were performed under an inert atmosphere (nitrogen).

Example 1: Preparation of a Catalyst System (1)

The alumino-pyrrole compound (B1, 81 mg, 0.45 mmol) synthesized in Preparation Example 4 was dissolved in methylcyclohexane (1 ml) and a resultant mixture was fed into a 1-neck flask. In addition, triethylaluminum (137 mg, 1.20 mmol) and diethylaluminum chloride (145 mg, 1.20 mmol) were dissolved in methylcyclohexane (2 ml) and then fed into the 1-neck flask, thereby preparing a mixture.

The chromium compound (Formula 1a, 53 mg, 0.15 mmol) prepared in Preparation Example 1 was dissolved in methylcyclohexane (1 ml) and then added to the mixture, followed by allowing reaction. As a result, a catalyst system was prepared as a dark green transparent solution in which hardly any precipitate was present (concentration: 63 mmol chromium/g-solution).

Example 2: Preparation of Catalyst System (2)

A catalyst system was prepared as a dark green transparent solution in the same manner as in Example 1, except that the chromium compound (Formula 1b) prepared in Preparation Example 2 was used instead of the chromium compound (Formula 1a) prepared in Preparation Example 1 (concentration: 63 mmol chromium/g-solution).

Example 3: Preparation of Catalyst System (3)

The chromium compound (Formula 1c, 110 mg, 0.30 mmol) prepared in Preparation Example 3 was dissolved in toluene (3 ml). Subsequently, 2,5-dimethylpyrrole (86 mg, 0.90 mmol) was added thereto and a temperature was lowered to 0° C. To a resultant mixture, a toluene solution (2 ml) in which triethylaluminum (377 mg, 3.30 mmol) and diethylaluminum chloride (289 mg, 2.40 mmol) were dissolved and mixed was slowly added. When reaction was allowed at 0° C. for one hour, a dark yellow solution in which hardly any precipitate was present was formed. It could be confirmed that, after temperature was highly elevated, the dark yellow solution changed into a dark orange solution (concentration: 50 μmol chromium/g-solution).

Example 4: Preparation of Catalyst System (4)

The alumino-pyrrole compound (B1, 81 mg, 0.45 mmol) represented by Formula 5 (R$^2$=ethyl group, R$^3$=R$^6$=methyl group, R$^4$=R$^5$=hydrogen) synthesized in Preparation Example 4 was dissolved in methylcyclohexane (1 ml) and was fed into a 1-neck flask. Triethylaluminum (137 mg, 1.20 mmol) and diethylaluminum chloride (145 mg, 1.20 mmol) were dissolved in methylcyclohexane (2 ml) and fed into the 1-neck flask, thereby preparing a mixture. The chromium compound (Formula 1c, 55 mg, 0.15 mmol) prepared in Preparation Example 3 was dissolved in methylcyclohexane(1 ml) and added to the prepared mixture, followed by allowing reaction. As a result, a catalyst system was prepared as a dark green transparent solution in which a precipitate was hardly present (concentration: 50 mmol chromium/g-solution).

Example 5: Preparation of Catalyst System (5)

Figure 4:
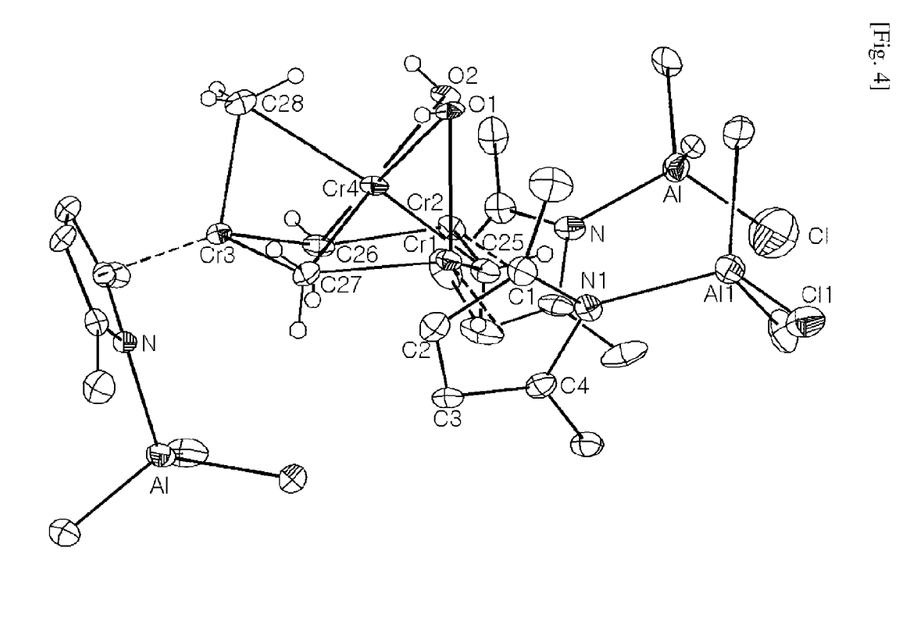
FIG. 4 illustrates a single-crystal X-ray diffraction analysis result of an intermediate compound obtained by a catalyst system prepared according to Example 5 of the present invention.

A catalyst system was prepared in the same manner as in Example 4, except that the alumino-pyrrole compound represented by Formula 5 (B2, R$^2$=methyl group, R$^3$=R$^6$=methyl group, R$^4$=R$^5$=hydrogen) prepared in Preparation Example 5 was used instead of the alumino-pyrrole compound represented by Formula 5 (B1, R$^2$=ethyl group, R$^3$=R$^6$=methyl group, R$^4$=R$^5$=hydrogen) prepared in Preparation Example 4, and trimethylaluminum and dimethylaluminum chloride were used instead of triethylaluminum and diethylaluminum chloride (concentration: 50 μmol chromium/g-solution). When the prepared catalyst system was stored for one month at room temperature, a single crystal of a reaction intermediate was partially precipitated. The structure of the precipitated single crystal was analyzed by an X-ray diffraction method. As a result, a cluster compound composed of four chromium atoms was determined as illustrated in FIG. 4.

Example 6: Preparation of Catalyst System (6) Including Catalyst Precursor

The compound (10 mg, 25.5 μmol) represented by Formula 2 (P1, R$^2$=X=methyl group, R$^3$=R$^6$=methyl group, $R^4=R^5$=hydrogen) synthesized in Preparation Example 6 was added to methylcyclohexane (0.3 ml) in a 1-neck flask. Triethylaluminum (137 mg, 1.20 mmol) and diethylaluminum chloride (145 mg, 1.20 mmol) were dissolved in methylcyclohexane (0.7 ml) and then fed into the 1-neck flask. As a result, a catalyst system was prepared as a dark green transparent solution (concentration: 50 µmol chromium/g-solution).

Example 7: Preparation of Catalyst System (7) Including Catalyst Precursor

A catalyst system was prepared as a dark green transparent solution in the same manner as in Example 6, except that the compound represented by Formula 2 (P2, $R^2$=ethyl group, X=chlorine, $R^3=R^6$=methyl group, $R^4=R^5$=hydrogen) prepared in Preparation Example 7 was used instead of the compound represented by Formula 2 (P1, $R^2$=X=methyl group, $R^3=R^6$=methyl group, $R^4=R^5$=hydrogen) prepared in Preparation Example 6 (concentration: 50 µmol chromium/g-solution).

Comparative Example 1: Preparation of Catalyst System of Philips

According to a method disclosed in U.S. Pat. No. 5,856, 257, a catalyst system was prepared. Tris(2-ethyl hexanoate) chromium (III) (Cr(EH)$_3$) (145 mg, 0.30 mmol) was dissolved in toluene (3 ml). Subsequently, 2,5-dimethylpyrrole (86 mg, 0.90 mmol) was added thereto and a temperature was lowered to 0° C. To the resultant mixture, a toluene (2 ml) solution in which triethylaluminum (377 mg, 3.30 mmol) and diethylaluminum chloride (289 mg, 2.40 mmol) were dissolved and mixed was slowly added. When reaction was allowed at 0° C. for one hour, a black precipitate was formed. The formed precipitate was removed through filtration, thereby obtaining a transparent dark orange catalyst system solution (concentration: 50 mmol chromium/g-solution).

Comparative Example 2: Preparation of Catalyst System of Philips

A catalyst system was prepared in the same manner as in Comparative Example 1, except that chromium (III) (Cr(EH)3) manufactured by the same company but having a different serial number was used.

Comparative Example 3: Preparation of Catalyst System

A catalyst system was prepared in the same manner as in Comparative Example 1, except that methylcyclohexane, instead of toluene. A black precipitate was filtered and thus a catalyst system was prepared as a dark green solution (concentration: 50 mmol chromium/g-solution).

Example 8: Ethylene Trimerization Reaction Using Catalyst System of Example 3

Methylcyclohexane (20 ml) and triethylaluminum (0.024 mmol), as scavengers, were fed into a high-pressure polymerization reactor in a dry box. Subsequently, the high-pressure polymerization reactor was taken out of the dry box and the temperature thereof was elevated to 90° C. The catalyst system (0.25 µmol) prepared in Example 3 was weighed and methylcyclohexane was added thereto, such that a total volume of a resultant solution became 2 ml. Since the catalyst was used in a very small amount, triethylaluminum (8 equivalents with respect to chromium) and diethylaluminum chloride (8 equivalents with respect to chromium) were added thereto as scavengers, and then a catalyst solution was aspirated by a syringe and injected into the reactor. Subsequently, ethylene was injected at a pressure of 50 bar and polymerization was performed for 30 minutes. The temperature of the reactor was rapidly lowered and then an ethylene gas was vented and removed from the reactor. 5 ml of ethanol and 5 ml of 10% hydrochloric acid were added to the reactor, thereby terminating the reaction. A portion of a resultant sample was taken and subjected to gas chromatography. The amount of 1-hexene generated through the gas chromatography was measured. In addition, the amount of a solid-type polymer formed by filtering the entire resultant solution was measured. A result is summarized in Table 1 below.

Example 9 to 12: Ethylene Trimerization Reaction Using Catalyst System of Each of Examples 4 to 7

Ethylene polymerization (trimerization) was carried out in the same manner as in Example 8, except that the catalyst system prepared in each of Examples 4 to 7, instead of the catalyst system prepared in Example 3, was weighed and used in an amount summarized in Table 1 (0.25 µmol to 1.00 µmol). After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 1 below.

Example 13: Ethylene Trimerization Reaction Using Catalyst System of Example 1

Ethylene polymerization (trimerization) was carried out in the same manner as in Example 8, except that the catalyst system prepared in Example 1 was used in an amount of 0.250 µmol. After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 1 below.

Example 14: Ethylene Trimerization Reaction Using Catalyst System of Example 2

Ethylene polymerization (trimerization) was carried out in the same manner as in Example 8, except that the catalyst system prepared in Example 2, instead of the catalyst system prepared in Example 1, was used in an amount of 0.50 µmol. After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 1 below

Comparative Example 4: Ethylene Trimerization Reaction Using Catalyst System of Comparative Example 1

Methylcyclohexane (20 ml) and triethylaluminum (0.024 mmol) were fed into a high-pressure polymerization reactor in a dry box as scavengers. Subsequently, the high-pressure polymerization reactor was taken out of a dry box and the temperature thereof was elevated to 90° C. The catalyst system (solution, 1.00 µmol) prepared in Comparative Example 1 was weighed and taken and methylcyclohexane was added thereto, such that a total volume of a resultant solution became 2 ml. A catalyst solution was aspirated by a syringe and injected into the reactor. Subsequently, ethylene was injected at a pressure of 50 bar and polymerization was performed for 30 minutes. The temperature of the reactor was rapidly lowered and then an ethylene gas was vented and removed from the reactor. 5 ml of ethanol and 5 ml of 10% hydrochloric acid were added to the reactor, thereby terminating the reaction. A portion of a resultant sample was taken and subjected to gas chromatography. The amount of 1-hexene generated through the gas chromatography was measured. In addition, the amount of a solid-type polymer formed by filtering the entire resultant solution was measured. A result is summarized in Table 2 below.

Comparative Example 5: Ethylene Trimerization Reaction Using Catalyst System of Comparative Example 2

Ethylene polymerization (trimerization) was performed in the same manner as in Comparative Example 4, except that the catalyst system solution prepared in Comparative Example 2 was used instead of the catalyst system prepared in Comparative Example 1. After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 2 below.

Comparative Example 6: Ethylene Trimerization Reaction (2) Using Catalyst System of Comparative Example 1

Ethylene polymerization (trimerization) was performed in the same manner as in Comparative Example 4, except that the catalyst system prepared in Comparative Example 1 was used in an amount of 2.00 µmol. After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 2 below.

Comparative Example 7: Ethylene Trimerization Reaction Using Catalyst System of Comparative Example 3

Ethylene polymerization (trimerization) was performed in the same manner as in Comparative Example 4, except that the catalyst system prepared in Comparative Example 3 was used in an amount of 2.00 µmol. After terminating the reaction, a portion of a sample was taken and subjected to gas chromatography. The amount of 1-hexene generated through the gas chromatography was measured. In addition, the amount of a solid-type polymer formed by filtering the entire resultant solution was measured. A result is summarized in Table 2 below.

Preparation Example 8: Preparation of Chromium Compound Having Structure Represented by Formula 1

An experiment was performed in the same manner as in Preparation Example 3, except that 2,2-dimethylpropionic acid was used instead of 2-ethylhexanoic acid. After synthesizing a compound, vacuum suction was performed at 120° C. As a result, a solvent and 2,2-dimethylpropionic acid, as a by-product, were removed and a gel-type product was obtained.

Preparation Example 9: Preparation of Chromium Compound Having Structure Represented by Formula 1

An experiment was performed in the same manner as in Preparation Example 1, except that heptanoic acid was used instead of 2-ethylhexanoic acid. After synthesizing a compound, vacuum suction was performed at 120° C. As a result, a solvent and heptanoic acid, as a by-product, were removed and a gel-type product was obtained.

Preparation Example 10: Preparation of Chromium Compound Having Structure Represented by Formula 1

An experiment was performed in the same manner as in Preparation Example 1, except that benzoic acid was used instead of 2-ethylhexanoic acid. During a reaction process, a navy blue gel was obtained.

Preparation Example 11: Preparation of Chromium Compound Having Structure Represented by Formula 1

An experiment was performed in the same manner as in Preparation Example 1, except that cyclohexanecarboxylic acid was used instead of 2-ethylhexanoic. During a reaction process, a navy blue gel was obtained.

Property Evaluation Methods (1) Activity (unit: Kg(1-hexene)/g(catalyst(Cr))/hr): After measuring the mass of obtained 1-hexene, activity was obtained by dividing the measured mass by the amount of an added catalyst.

(2) Stability evaluation of compound: the compound prepared in each of Preparation Example 1 and Preparation Example 3 was dissolved in xylene and then refluxed at 160° C. for 10 hours to evaluate stability

TABLE 1

| | Examples | | | | | | |
|---|---|---|---|---|---|---|---|
| | 8 | 9 | 10 | 11 | 12 | 13 | 14 |
| Catalyst system | Example 3 | Example 4 | Example 5 | Example 6 | Example 7 | Example 1 | Example 2 |
| Amount of catalyst (µmol) | 0.25 | 0.25 | 1.00 | 1.00 | 1.00 | 0.25 | 0.50 |
| Amount of obtained 1-hexene (g) | 6.9 | 7.1 | 5.6 | 12.4 | 6.4 | 7.1 | 9.6 |

TABLE 1-continued

| | Examples | | | | | | |
|---|---|---|---|---|---|---|---|
| | 8 | 9 | 10 | 11 | 12 | 13 | 14 |
| Activity (Kg(1-hexene)/g(Cr)/h) | 1,070 | 1,100 | 220 | 500 | 260 | 1,100 | 770 |
| Dimer C4 (wt %) | 4.26 | 0.70 | 0.24 | 3.21 | 0.86 | 0.01 | 0.10 |
| Trimer C6 (wt %) | 88.08 | 94.12 | 92.38 | 88.08 | 93.60 | 93.06 | 93.14 |
| Tetramer C8 (wt %) | 0.29 | 0.48 | 0.39 | 0.39 | 0.32 | 0.48 | 0.35 |
| Pentamer C10 (wt %) | 7.37 | 4.70 | 6.99 | 8.32 | 5.22 | 5.50 | 6.41 |
| Content of 1-hexene in trimer (wt %) | 99.21 | 98.42 | 98.77 | 98.2 | 98.56 | 98.98 | 99.07 |
| Amount of obtained PE (mg) | 27 | 27 | 35 | 17 | 6 | 27 | 28 |

TABLE 2

| | Comparative Examples | | | |
|---|---|---|---|---|
| | 4 | 5 | 6 | 7 |
| Catalyst system | Comparative Example 1 | Comparative Example 2 | Comparative Example 1 | Comparative Example 3 |
| Amount of catalyst (μmol) | 1.00 | 1.00 | 2.00 | 2.00 |
| Amount of obtained 1-hexene (g) | 7.2 | 3.2 | 15.1 | 11.9 |
| Activity (Kg (1-hexene)/g (Cr)/h) | 280 | 120 | 290 | 230 |
| Dimer C4 (wt %) | 0.52 | 1.00 | 0.01 | 0.03 |
| Trimer C6 (wt %) | 92.97 | 93.04 | 92.08 | 92.36 |
| Tetramer C8 (wt %) | 0.38 | 0.64 | 0.34 | 0.41 |
| Pentamer C10 (wt %) | 6.08 | 5.33 | 7.57 | 7.20 |
| Content of 1-hexene in trimer (wt %) | 98.85 | 97.78 | 98.51 | 99.01 |
| Amount of obtained PE (mg) | 32 | 11 | 25 | 28 |

From these results, it can be confirmed that the catalyst systems of Examples 8 to 14 including the chromium compound represented by Formula 1 or the chromium-based catalyst precursor represented by Formula 2 exhibit similar or greatly increased catalytic activity (up to four times) compared to the catalyst systems of Comparative Examples 4 to 7 using Cr(EH)$_3$, whereby the cost of a catalyst can be greatly reduced.

In particular, activity degrees in Examples 8, 9, 13, and 14 including the chromium compound represented by Formula 1 of the present invention are remarkably high, compared to Comparative Examples 4 to 7 using Cr(EH)$_3$.

In Examples 10 to 12, activity, an attainment rate of a trimer, the content of 1-hexene in the trimer, and the like are similar to those of Comparative Example 4 to 7, but a removal process of an aromatic hydrocarbon solvent is not required. In addition, the unit cost of a raw material is low and economic efficiency is superior. In particular, in the cases of Example 10 to 12, a catalyst is used in a much smaller amount, but when comparing Examples 10 to 12 and Comparative Examples 6 and 7, a similar result is exhibited.

From these results, it can be confirmed that, in the cases of the catalyst systems of Example 8 to 14, a catalyst may be prepared in an aliphatic hydrocarbon solvent, an aromatic hydrocarbon solvent removal process of trimerizing ethylene in the aliphatic hydrocarbon solvent is not required, and a filtration process is not required since a precipitate is not generated upon preparation of the catalyst. Accordingly, it can be confirmed that a preparation process of the catalyst system is simple and may be easily performed.

In addition, when the stabilities of the compounds of Preparation Example 1 and Preparation Example 3, in which the chromium compound according to the present invention is prepared, are compared, it can be confirmed that the stability of the compound of Preparation Example 3 is superior compared to that of the compound of Preparation Example 1. From this result, it can be confirmed that both catalyst systems including the chromium compounds of Preparation Example 1 and Preparation Example 3 exhibit high catalytic activity, but the chromium compound having the structure represented by Formula 1c prepared in Preparation Example 3 exhibits higher stability. In particular, it can be confirmed that the chromium compound of Preparation Example 3 exhibits superior solubility with respect to a hydrocarbon solvent and thus has very suitable characteristics for being applied to the catalyst system.

In addition, through Preparation Example 8 to 11, preparation of various embodiments of the chromium compound represented by Formula 1 included in the present invention were confirmed.

Those of ordinary skill in the art may easily carry out simple applications and modifications based on the foregoing teachings within the scope of the present invention, and these modified embodiments may also be within the scope of the present invention.

The invention claimed is:
1. A catalyst for polymerizing olefins, comprising a reaction product of:
   a chromium compound represented by Formula 1c below;
   an aluminum compound represented by Formula 3 below; and
   an alumino-pyrrole compound represented by Formula 5 below:

[{CH$_3$(CH$_2$)$_3$CH(CH$_2$CH$_3$)CO$_2$}$_2$Cr(OH)]$_4$·2H$_2$O;  [Formula 1c]

(R$^2$)$_n$Al(X$^2$)$_{3-n}$,  [Formula 3]

wherein R$^2$ is a C$_1$ or C$_2$ hydrocarbon group, X$^2$ is a halogen atom, and an average value of n is 1 to 3; and

[Formula 5]

wherein R$^2$ is a C$_1$ or C$_2$ hydrocarbon group and R$^3$, R$^4$, R$^5$, and R$^6$ are each independently a hydrogen atom or a C$_1$ or C$_2$ alkyl group, wherein the compound of Formula 1c is obtained by the method of Preparation Example 3.

2. The catalyst according to claim 1, wherein the aluminum compound is a mixture of triethylaluminum (Et$_3$Al) and diethylaluminumchloride (Et$_2$AlCl), the alumino-pyrrole compound is a compound represented by Formula 5 wherein R$^2$ is an ethyl group, R$^3$ and R$^6$ are methyl groups, and R$^4$ and R$^5$ are hydrogen atoms.

3. The catalyst according to claim 1, wherein, in the catalyst system, a molar ratio of the chromium compound to the aluminum compound (Cr:Al) added upon preparation (reaction) is 1:10 to 1:50.

4. The catalyst according to claim 1, wherein, in the catalyst system, a molar ratio of the chromium compound to the alumino-pyrrole compound (chromium compound:alumino-pyrrole compound) added upon preparation (reaction) is 1:1 to 1:5.

5. The catalyst according to claim 1, wherein the catalyst system further comprises an aliphatic hydrocarbon solvent.

* * * * *